US00PP09645P

United States Patent [19]

Van Leuven

[11] Patent Number: Plant 9,645

[45] Date of Patent: Sep. 24, 1996

[54] APPLE TREE NAMED 'MYRA'

[75] Inventor: Myles Van Leuven, Kennewick, Wash.

[73] Assignee: Columbia & Okanagan Nursery, Wenatchee, Wash.

[21] Appl. No.: 514,457

[22] Filed: Jul. 6, 1995

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

P.P. 9,298 9/1995 Fukuda ..... Plt./34.1

P.P. 9,508 4/1996 Lynd ..... Plt./34.1

*Primary Examiner*—James R. Feyrer

*Attorney, Agent, or Firm*—Klarquist Sparkman Campbell Leigh & Whinston

[57] ABSTRACT

A new and distinct variety of Fuji apple tree (*Malus pumila*) named 'Myra' characterized by (1) fruit having a bright pinkish red color extending uniformly over substantially the entire body of the fruit and overlain with slightly darker pinkish-red stripes; and (2) early fruit coloring and (3) earlier fruit maturation than the popular commercially planted red striped Fuji strains.

5 Drawing Sheets

BACKGROUND OF THE INVENTION

The present invention comprises a new and distinct variety of apple tree (*Malus pumila*), referred to by the varietal name, 'Myra'.

The parent tree of the new variety was a whole tree mutation of one of several strains of an unknown red strain of the Fuji variety (not patented) and discovered in a cultivated area in Penticton, British Columbia, Canada. The fruit carried by the tree had an attractive color, a bright pinkish red that extends uniformly over substantially the entire body of the fruit, that is distinct from that of any of the known Red Fuji striped strains, e.g., TAC 114 (U.S. Plant Pat. No. 8,032), Naga-fu 6 (not patented), and BC-2 (also known as Moriho-fu #2, not patented). The variety exhibits advanced color development of 14 days over that of Standard Fuji and its known red striped strains. In addition, the fruit of this variety also exhibits an advanced maturity of seven days as exhibited by the development of watercore around the vascular bundles.

The predomenant strains of red striped Fuji apple in commercial production today are, in order of importance (i.e., acreage): BC 2 (also known as Moriho-fu 2, not patented) a selection arriving from British Columbia, Canada and the first known legal red striped strain in the United States; TAC 114 (U.S. Plant Pat. No. 8,032); and Naga-fu 6 (not patented), a Japanese selection entering the United States through the IR-2 tree fruit bud wood importation program at Washington State University's Irrigated Agriculture Research and Extension Center, Prosser, Wash. Numerous other red striped sports of Fuji are known and some have seen limited commercial plantings. Although some Fuji strains do mature earlier than the standard Fuji maturity timing exhibited by the predominant strains above, such as Yataka™ (U.S. Plant Pat. No. 7,001) and its red striped sport Beni Shogun (U.S. Plant Pat. No. 7,997), no Fuji strains are known to bear fruit having the distinctive bright pinkish red coloration at harvest exhibited by the Myra Fuji.

The Myra Fuji was compared to BC 2 Fuji, Naga-fu 6 Fuji and TAC-114. Fruit from all the strains were grown at Broetje Orchards, Prescot, Wash. and were from trees of similar age. Fruit from all the strains were sampled and compared at weekly intervals beginning on Sep. 12, 1994 and ending on Oct. 19, 1994. Samples were photographed on the tree and in a group off the tree. Maturity indices of pressure, °Brix, starch, and watercore development were also taken. Myra Fuji exhibits an earlier fruit color development of the overcolor and a very distinctive chroma and hue. Watercore developed around the vascular bundles in Myra Fuji at least a week ahead of the other Fuji apple strains tested. Although TAC 114 is claimed to exhibit an advanced maturity of 10–14 days over that of the standard date, this claim was not borne out by comparison testing. The internal maturity indices of pressure, °Brix, and starch did not exhibit appreciable differences between Myra Fuji and the other strains. Thus, both the color development of Myra Fuji and its watercore development substantiate the claim for an earlier maturity over that of the other compared strains.

This invention has not been observed under all possible environmental conditions. However, the following combination of trains have been repeatedly observed in asexually propagated progeny and are determined to be the basic characteristics of this invention, which in combination distinguish this variety of Fuji apple as a new and distinct variety: (1) fruit having a bright pinkish red color extending uniformly over substantially the entire body of the fruit and overlain with slightly darker pinkish-red stripes; (2) fruit color development approximately 14 days earlier than Standard Fuji and the predominant red striped strains; and (3) fruit maturation approximately seven days earlier than the popular commercially planted red striped Fuji strains as shown by the development of watercore around the vascular bundles.

The new variety is readily identified as Myra Fuji apple by the uniformity of these characteristics. To the inventor's knowledge, this combination of characteristics distinguish this new variety from all other varieties of Fuji apple of which I am aware.

Asexual reproduction through two generations on several trees shows that these characteristics are established and transmitted through succeeding asexual propagations.

BRIEF DESCRIPTION OF THE PHOTOGRAPHS

Figure 1:
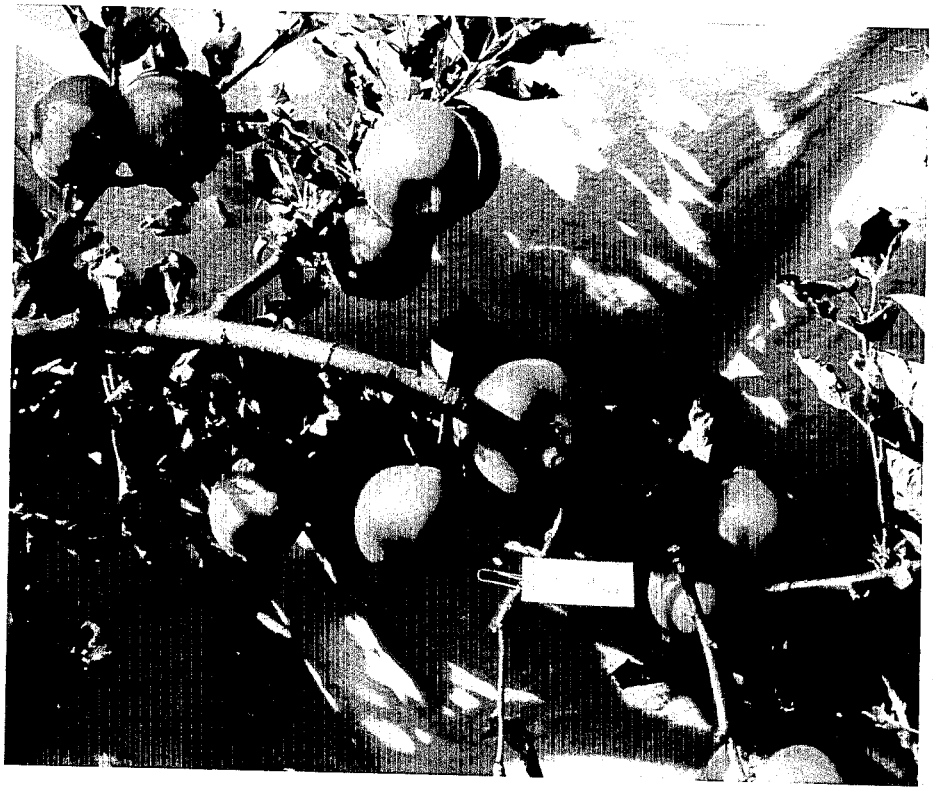
FIG. 1 is a view of a fruiting limb of Myra Fuji from a sixth leaf third generation tree. The photograph was taken at the first picking date and exhibits the bright pinkish red coloration of the fruit in both its striping and overcolor.
Figure 2:
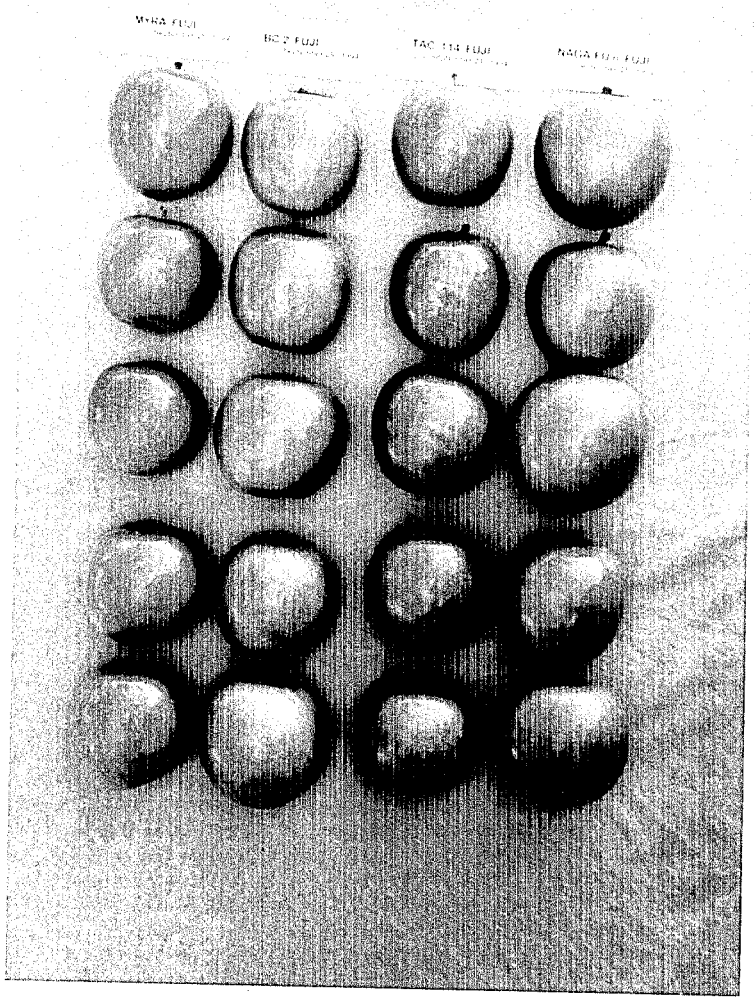
FIG. 2 is a view of fruit from the Myra, BC 2, TAC-114, and Naga-fu 6 Fuji strains showing the advanced color development of the Myra Fuji strain. The photograph was taken Sep. 28, 1994, two weeks prior to the first picking of Myra Fuji and three weeks prior to the first picking of the BC 2, TAC 114 and Naga-fu 6 Fuji strains, all grown at the Broetje Orchards, Prescott, Wash.
Figure 3:
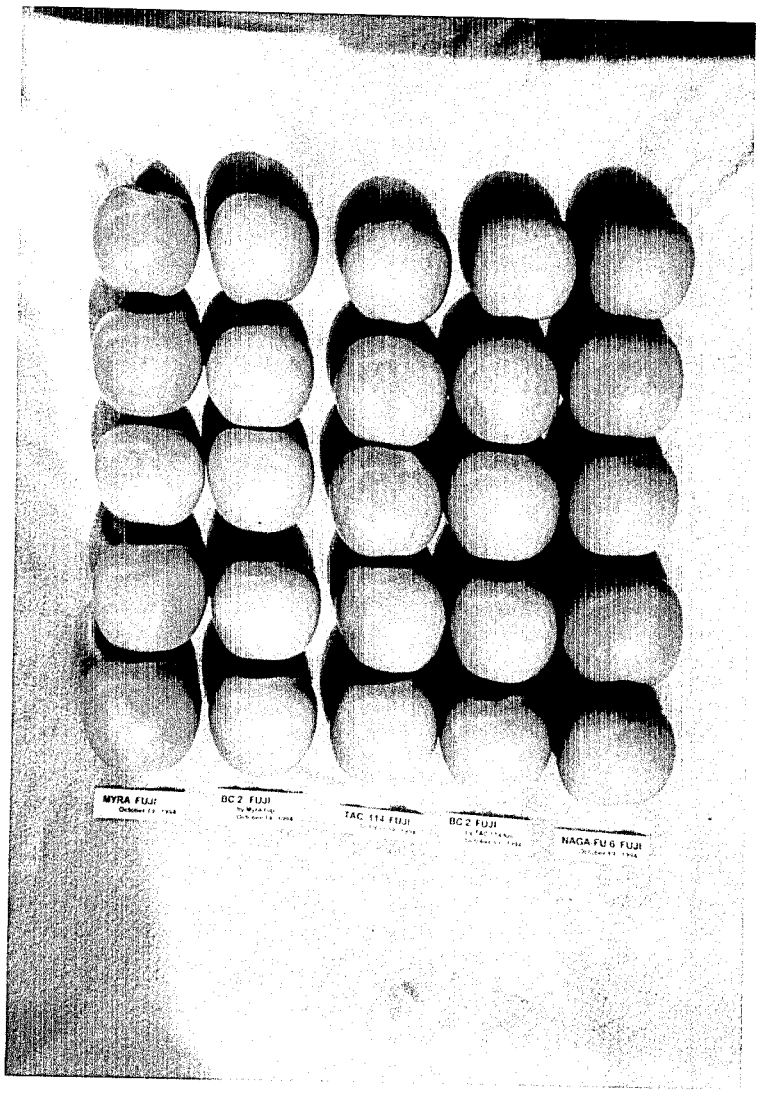
FIG. 3 is a view of the shaded back side of fruit from samples of harvest maturity of the following Fuji strains (from left to right) Myra, BC 2 (by Myra), TAC 114, BC 2 (by TAC 114), and Naga-fu 6, showing that Myra fruit display a greater uniformity of color and that substantially the entire surface area of the Myra fruit is covered by bright pinkish red coloration.
Figure 4:
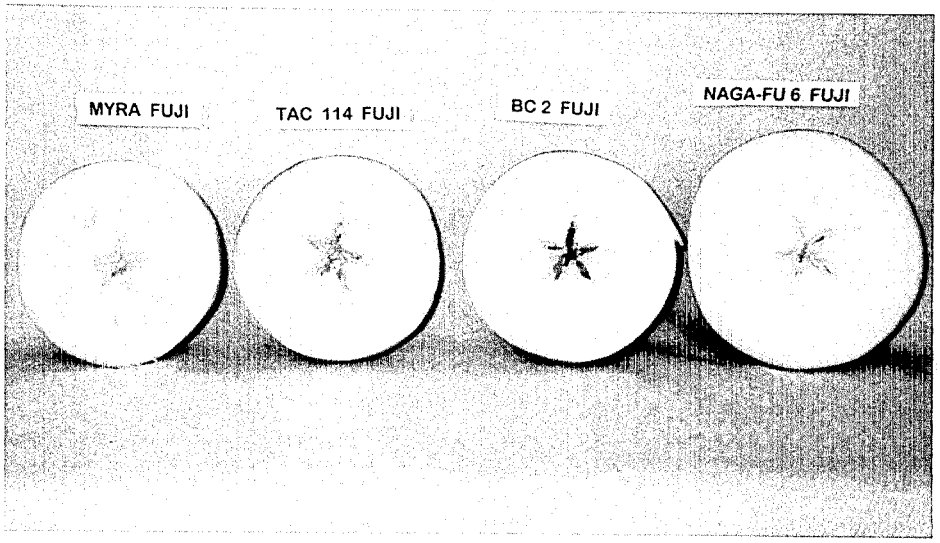
FIG. 4 is a view of tangential sectioned fruit of Myra, TAC 114, BC 2, and Naga-fu 6 Fuji taken on Oct. 12, 1994, the date of the first picking of Myra Fuji, showing the development of watercore around the vascular bundle area (an indication of Fuji fruit maturity development) of Myra Fuji grown at the Broetje Orhcards, Prescott, Wash.
Figure 5:
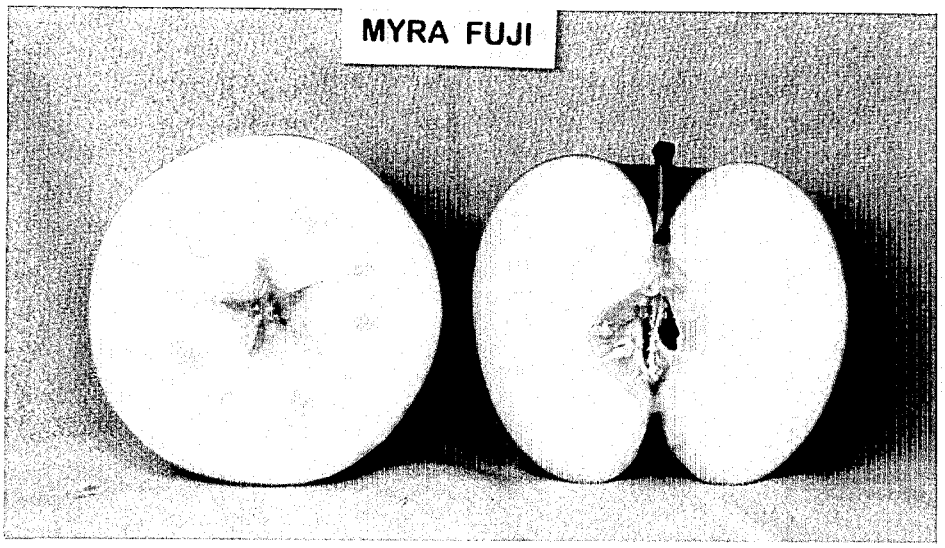
FIG. 5 is a view of fruit sections of Myra Fuji illustrating the core area as seen both tangentially and longitudinally at harvest maturity.
Figure 6:
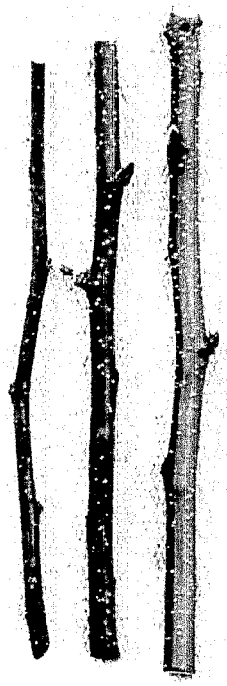

FIG. 6 is a view of Myra Fuji bark appearance of one to three year old branches: Left, one year old; Middle, two year old; Right, three year old.

DETAILED DESCRIPTION

The following is a detailed description of the invention based on plants produced under commercial practices in Prescott, Wash. and observed at this location in October, 1994. All trees were of eating ripe maturity, which, in the case of the Fuji variety, is also harvest maturity.

Color references are made in accordance with the Munsell Color Cascade except where general color terms of ordinary dictionary significance is obvious.

All trees of the new variety, insofar as I have been able to observe them, have been identical in all the characteristics described below. Other than as set forth below, as of this time I have not observed any other characteristics which are different from seedling Fuji apple trees.

Comparison Tables

The following comparison tables provide comparisons of fruit color and fruit watercore development for four varieties of Fuji apple: Myra, BC 2, TAC 114, and Naga-fu 6.

The colorimetric data is a measurement from two different instruments. L, a, and b readings represent three scales of color obtained using an instrument from Hunter Lab, 11491 Sunset Hills Road, Reston, Va. Together the three scales represent a three-dimensional color model with the three axis represented as follows: L axis numbers represent the colors of white to black with white equal to a reading of 100 and black equals 0; a axis numbers that are positive (+) represent the reds with the higher the number being redder; b axis numbers that are positive (+) represent the yellows with the higher the number the greater the yellow. Each fruit reading was an average of three readings taken from three equal distant quadrants. The % Red/Green reading is a percentage ratio measurement of the red to green colors only using an Agtron Model E5-W by Magnuson Engineers, Inc.

COLOR CHART COMPARISON - FRUIT

| | Myra | BC 2 | TAC 114 | Naga-fu 6 |
|---|---|---|---|---|
| 10/12/94 (sample date) | | | | |
| Groundcolor | 23-3 | 24-4 | 23-2/23-3 | 25-2 |
| Undercolor | 39-10 | 35-12 | 36-11 | 35-13 |
| Stripe | 39-12/ 39-13 | 35-14 | 36-13 | 35-14 |
| 10/19/94 (sample date) | | | | |
| Groundcolor | 25-3 | 26-2 | 25-3 | 23-2 |
| Undercolor | 40-11 | 38-7 | 33-4 | 33-10 |
| Stripe | 41-12 | 38-12 | 37-14 | 35-14 |

COLORIMETRIC COMPARISON - FRUIT

| | Myra | BC 2 | TAC 114 | Naga-fu 6 |
|---|---|---|---|---|
| 10/12/94 (sample date) | | | | |
| L | 39.93 | 43.84 | 45.22 | 43.64 |
| a | +25.43 | +17.14 | +13.72 | 12.38 |
| b | +12.16 | +15.06 | +15.92 | 15.36 |
| % Red/Green | 87.1 | 81.8 | 78.7 | 73.3 |
| 10/19/94 (sample date) | | | | |
| L | 36.85 | 42.14 | 43.24 | 39.65 |
| a | +28.96 | +22.14 | +18.22 | +18.96 |
| b | +11.04 | +13.64 | +14.97 | +13.01 |
| % Red/Green | 91.3 | 84.9 | 81.8 | 83.1 |

WATERCORE DEVELOPMENT COMPARISON - FRUIT

| | Myra | BC 2 | TAC 114 | Naga-fu 6 |
|---|---|---|---|---|
| 10/06/94 (sample date) | | | | |
| 0 cm diameter | 6* | 9 | 10 | 10 |
| 0.1 cm diameter | 1 | 1 | 0 | 0 |
| 0.2 cm diameter | 3 | 0 | 0 | 0 |
| 10/12/94 (sample date) | | | | |
| 0 cm diameter | 0 | 6 | 6 | 10 |
| 0.1 cm diameter | 1 | 4 | 4 | 0 |
| 0.2 cm diameter | 5 | 0 | 0 | 0 |
| 0.5 cm diameter | 4 | 0 | 0 | 0 |
| 10/19/94 (sample date) | | | | |
| 0 cm diameter | 0 | 3 | 3 | 6 |
| 0.1 cm diameter | 0 | 3 | 3 | 1 |
| 0.2 cm diameter | 2 | 2 | 2 | 3 |
| 0.5 cm diameter | 3 | 2 | 2 | 0 |
| 1 cm diameter | 5 | 0 | 0 | 0 |

* = the number of fruit samples exhibiting that diameter of water core around the vascular bundles.

Propagation: Holds to distinguishing characteristics through succeeding propagation by rooted cuttings.

Locality where grown and observed: Broetje Orchards, Prescott, Wash.

Tree: Medium, vigorous, spreading, low, round-topped, slow growing, hardy, productive, regular bearer.

*Trunk.*—Medium, smooth. Mouse gray in color.

*Branches.*—Medium thick, smooth, much branching.

*Lenticels.*—Medium number; medium large; One year old color #28–15, two year old color #33–15, three year old color #35–16 of the Munsell Limited Color Cascade.

*Leaves.*—Length 3.5 inches; Width 2.0 inches; medium large, medium wide, medium long, acute; gently undulating; upward-folding; Color #21–14 of the Munsell Limited Color Cascade. Margin: Serrate.

*Flower.*—Mid-Season. Side: Medium. Color: White with light pink on margins and reverse side.

Fruit: Maturity when described was eating ripe.

*Size.*—Medium to medium large; globose with inclination to oblate; irregular.

*Cavity.*—Symmetrical; abrupt at base; acute; smooth with some inclination for light russet.

*Basin.*—Symmetrical; medium depth; wide; medium breadth; sloping; markings none.

Stem: Medium stout to stout; medium length—½" to +e,fra /8+ee ".

Calyx: Persistent, closed.

*Segments.*—United at base; broadly lanceolate.

*Outer surface.*—Pubescent.

*Inner surface.*—Pubescent.

Eye: Erect convergent, recurved at apex.

Skin: Medium thin; smooth; waxed; glossy.

*Dots.*—Many; small but conspicuous; elliptical; moderately rough.

*Color of dots.*—Color #29–1 of the Munsell Limited Color Cascade.

*Ground color.*—Color #23–3 of the Munsell Limited Color Cascade.

*Color markings.*—Striped

*Color of markings.*—Undercolor #39–10, stripes #39–12/39–13 of the Munsell Limited Color Cascade.

*Bloom.*—Moderate. Approximately 60–70 percent of outermost part of bloom is pink, shading to white at center. By contract, bloom of normal Fuji (BC-2 with Malling 9 root stock) is approximately 25 percent pink, shading to white at center. Blooming is 3–5 days ahead of normal Fuji.

*General color effect.*—Fruit—very attractive and pleasing color appearance with subtle, but distinct, darker striping overlaying overcolor.

*Flesh.*—Light creamy-yellow; juicy. Texture: Fine; firm; melting. Flavor: Sweet, mild-subacid, faintly aromatic. Quality: Best.

*Core.*—Open; position medium; size medium. Bundle area: Small, oblate (longitudinal section). Bundles: Moderately inconspicuous; in one whorl. Core lines: Basal clasping. Calyx-tube: Cone shaped. Stiles: Present. Stamens: Medium position; one distinct whorl. Seed cells: Open; slightly elliptical; tufted. Cell walls: Thin.

*Seeds.*—Number perfect: 10; generally acute point. Number in one cell: 2. Length: 9/32Δ. Breadth: 5/32Δ. Color: Color #30–16 of the Munsell Limited Color Cascade.

*Use.*—Market, culinary, dessert.

*Keeping quality.*—Long, up to 12 months in CA storage.

*Resistance to.— Insects: Good. Diseases: Good.*

I claim:

1. A new and distinct variety of Fuji apple tree substantially as herein shown and described.

* * * * *

MYRA FUJI